United States Patent [19]

Gormus

[11] Patent Number: 4,693,967
[45] Date of Patent: Sep. 15, 1987

[54] MONITORING THERAPY RESULTS IN BODY SAMPLES OF RECEPTOR CELLS

[75] Inventor: Bobby J. Gormus, Covington, La.

[73] Assignee: Research Corporation, New York, N.Y.

[21] Appl. No.: 235,510

[22] Filed: Feb. 18, 1981

[51] Int. Cl.$^4$ ............... G01N 33/533; G01N 33/534; G01N 33/554
[52] U.S. Cl. .......................................... 435/7; 435/29; 436/501; 436/512; 436/513; 436/519; 436/821
[58] Field of Search .................... 424/1, 8, 12; 435/4, 435/7, 29, 810, 879; 23/230 B; 436/63, 64, 519, 512, 513, 501, 821

[56] References Cited

U.S. PATENT DOCUMENTS

| | | | |
|---|---|---|---|
| 3,673,410 | 6/1972 | Waite et al. | 424/1 |
| 4,146,604 | 3/1979 | Kleinerman et al. | 424/8 |
| 4,192,917 | 3/1980 | Zurawski | 424/12 |
| 4,223,005 | 9/1980 | Teodorescu et al. | 436/519 |
| 4,223,305 | 9/1980 | Teudorescu et al. | 435/7 |
| 4,247,536 | 1/1981 | Fruitstone et al. | 424/12 |

OTHER PUBLICATIONS

Gormus et al., "The Bacteria(B)–Antibody(A)–Complement(C) (BAC) Rosette Method for Detecting C3 Receptors (R): Binding Specificity and Capping of Human Peripheral Blood Lymphocyte C3R", *Cellular Immunology*, vol. 55, (1980), pp. 94–105.

Stanislawski et al., "Immunoenzymic Methods for the Study of Surface Bound Immunoglobulins in Mice", *Chem. Absts.*, vol. 85, No. 11, (1976), p. 399, Absts #76174k.

Ben-Bassat et al, "Changes in the Surface Membrane of Lymphocytes from Patients with Chronic Lymphocytic Leukemia and Malignant Lyphomas", *Chem. Absts.*, vol. 87, (1977), p. 459, Absts. #116056y.

*Primary Examiner*—Esther M. Kepplinger
*Attorney, Agent, or Firm*—Scully, Scott, Murphy & Pressure

[57] ABSTRACT

A diagnostic method and reagents for monitoring the efficacy of therapeutic treatment using the phenomenon of capping of cell membrane receptors, and is useful for relating receptor capping to clinical responses to therapy in patients with diseases, disorders, or malignancies involving cells that possess receptors. Therapeutic efficacy is determined by detecting receptors for activated substances, e.g., the third component of complement (C3), on cells having receptors therefor on the cell membrane surface, e.g., human lymphocytes, by the binding of an activated receptor substance, preferably labeled with a fluorescent or radioactive marker.

5 Claims, No Drawings

MONITORING THERAPY RESULTS IN BODY SAMPLES OF RECEPTOR CELLS

DESCRIPTION OF THE INVENTION

1. Technical Field of the Invention

This invention relates to a diagnostic method and reagents for monitoring the efficacy of therapeutic treatment using the phenomenon of capping of cell membrane receptors, and is useful for relating receptor capping to clinical responses to therapy in patients with diseases, disorders, or malignancies involving cells that possess receptors. Therapeutic efficacy is determined by detecting receptors for activated substances, e.g. the third component of complement (C3), on cells having receptors therefor on the cell membrane surface, e.g., human lymphocytes, by the binding of an activated receptor substance, preferably labeled with a fluorescent or radioactive marker.

2. Background Art

The phenomenon of capping is a normal function of many receptors on different types of normal cells; when such bound receptors are warmed, e.g., to 37° C., the receptors become mobile within the cell membrane and move to coalesce at one pole of the cell to form a capped configuration.

It is well known that lymphocytes from patients with chronic lympocytic leukemia (CLL) are impaired in their ability to support normal mobility of surface receptors within the cell membrane. For example, several reports have indicated that capping of peripheral blood lymphocyte (PBL) surface immunoglobulin (SIg) is impaired in CLL. Diminished capping of lymphocyte concanavalin A (Con A) receptors has also been reported in CLL patients. Other PBL membrane receptors reported to be deficient in capping ability in CLL patients include those for histocompatibility antigens (HLA) after binding anti-HLA antibody; antigens binding anti-lymphocyte serum; the lectins (plant proteins), including those of phytohemagglutinin and lentil and ricin lectins; and the activated third component of complement (C3).

Complement, which comprises a series of at least 10 serum proteins (including C1-C9), is known to combine with certain antigen-antibody complexes in a prescribed order during complement fixation, which results in the lysis of cells possessing the antigen, e.g., red blood cells or certain kinds of bacteria, by destroying the integrity of the cell membrane. Complement is present in mammalian sera, including human sera, but for convenience mouse sera is most frequently used as a source thereof, since mouse complement has the advantage of being non-lytic (even to erythrocytes) and of fully cross-reacting with human complement receptors. Other sources of complement, e.g., guinea pig, etc., can be used, either in purified form lacking the terminal lytic components or with cells not susceptible to lysis thereby, e.g. bacterial cells such as *Salmonella typhimurium* or *Salmonella typhi* (ST) rather than erythrocytes. Cells bearing activated complement on their surfaces are also well known in the art, and include but are not limited to mammalian erythrocytes, preferably sheep or bovine, bacteria such as gram negative bacteria, and yeasts, e.g. zymosan.

C3 can be activated by a wide variety of methods; e.g., virtually any antigen-antibody complex, any gram-negative bacteria, etc. are well known in the art to activate C3. While it is generally preferred that the activating substance be water insoluble, water-soluble substances such as bovine serum albumin antigen-antibody complexes can also be employed.

Mammalian leukocytes and other cells contain receptors specific to the activated third component of complement (C3) on the cell membrane and the binding of an antigen-antibody complex having activated C3 thereto, was reported by C. Bianco et al. in J. Exp. Med. 138: 702 (1970) to form rosettes, i.e., a random form of binding to complement-rosetting cell (CRC) membrane receptors by the corresponding agonist ligand is seen when the reagents are mixed in the cold, e.g., at 0°-4° C. While useful for obtaining a qualitative estimate of rosette formation, the use of erythrocytes in such a technique has the disadvantage of inherent difficulties in separating rosetted and non-rosetted C3 receptor cells (e.g., lymphocytes), making it difficult if not impossible to reproducibly prepare slides for identification and further study.

B. J. Gormus et al. first reported capping of C3 receptors in J. Immunol. 112: 770 (1974), noted its occurrence with mouse spleen lymphocytes in J. Immunol. 114: 1221 (1975), and reported that this capping is an active process which appears to be controlled by the cellular cytoskeletal-contractile system in J. Immunol. 124: 2747 (1980). Further studies relating to human peripheral lymphocytes have been reported in Cellular Immunology 55: 94–105 (1980), the contents of which are incorporated by reference herein, which characterized C3 receptor cap formation in normal humans and in chronic lymphotycic leukemia (CLL) patients and reported that CLL lymphocytes exhibit greatly reduced capping.

DISCLOSURE OF THE INVENTION

It has now been found that the receptor capping ability in patients having diseases, disorders, or malignancies involving such cells can vary in samples taken at different times from the same patient, and that this variation provides a method for monitoring the efficacy of therapy for resorting such cells to normal, e.g., CLL and lymphocytic lymphoma.

Accordingly, it is a general object of the present invention to provide an improved method and reagents for monitoring the efficacy of therapeutic treatment affecting body cells having receptor capping abilities.

Another object of the present invention is to provide a method for differential diagnosis of human lymphomas, chronic lymphocytic leukemia, and other disorders or malignancies which involve cells having membrane C3 receptors.

A further object of the present invention is to provide improved reagents and techniques for determining the capping ability of rosettes formed by reaction of an activated C3-bearing substance with cell membrane C3 receptors.

An additional object of the present invention is to provide reagents which are specific to C3b or C3d receptors.

A more particular object of the present invention is to provide a new method and reagents for the detection of Fc lymphocyte receptors.

Upon study of the specification and appended claims, further objects, features and advantages of the present invention will become more fully apparent to those skilled in the art to which this invention pertains.

BEST MODE FOR CARRYING OUT THE INVENTION

Briefly, the above and other objects, features and advantages of the present invention are attained in one aspect thereof by providing a method of relating receptor capping to clinical responses to therapy in a patient having a disease, disorder, or malignancy affecting body cells possessing said receptors, which comprises comparing the percentage capping of said patient's cells with a base line normal value and evaluating continuation of such therapy if said percentage is increasing and discontinuance of such therapy if said percentage is decreasing.

While applicable to a wide variety of receptors, the presently preferred embodiment of this invention relates to the C3 receptors and their evaluation in the therapy of lymphocytic diseases, which will accordingly be discussed in detail. The C3 receptor, like SIg, has been shown to be present on most B lymphocyte membranes. Since CLL is usually a B lymphocyte disorder, the C3 receptor can be used as a marker to identify the subpopulation of lymphocytes containing abnormal cells.

CRL are elevated in percentages and in absolute numbers in CLL, as has been reported from several laboratories. Capping of PBL C3 receptors is impaired in CLL; this also agrees with previous reports indicating that other CLL lymphocyte membrane receptors, including B-lymphocyte SIg, are impaired in capping ability. In accordance with the present invention, it has been found that the C3 receptor capping impairment varies in degree from one CLL patient to another, and that the variability is related to therapy and to the clinical response to therapy. CLL patients who were clinically refractory to ongoing chemotherapy were capable of insignificant C3 receptor capping (19 percent), compared to controls. Approximately 10–20 percent of PBL cell controls appear capped at time zero; this phenomenon has been consistently observed in C3 receptor capping studies utilizing mouse spleen lymphocytes and in both normal and CLL PBL. It appears possible that C3 receptors on a small number of CRL occur in an aggregated state in vivo in the absence of exogenously added ligand.

Patients who had never received therapy for CLL prior to this study capped only slightly better (31 percent). Patients who had received successful chemotherapy for CLL prior to the present study, but who were receiving no current therapy and who were clinically asymptomatic or stable, were able to form STM complex-C3 receptor caps on a mean of 45 percent of their CRL. This latter group of patients also possessed the largest total number (8,700/$\mu$l blood) of C3 receptor-STM complexes cap-forming CRL of any of the categories studies. As a group, the CLL patients capable of forming STM complex-C3 receptor caps on the highest percentage of their CRL were those who were currently receiving therapy at the time of study and who were showing favorable clinical responses. This group was capable of forming STM complex-C3 receptor caps on 55 percent of their CRL, and these patients also possessed significantly fewer absolute numbers of STM complex-C3 receptor cap-forming CRL (4,500/$\mu$l of blood) than the asymptomatic, previously treated group (8,700/$\mu$l), but did not differ from the groups of patients who were refractory to treatment (5,700/$\mu$l) or from those who had never received chemotherapy (6,200/$\mu$l).

Since normal human donors formed ST complex-C3 receptor caps on a mean of 70 percent of their peripheral blood CRL, it is obvious that even the group of CLL patients that was capable of the highest degree of capping was impaired in the percentage of CRL capable of ST complex-C3 receptor cap formation. However, due to elevated WBC, elevated percentages of PBL, and elevated numbers of CRL, most CLL patients possessed greater absolute numbers of CRL capable of ST complex-C3 receptor cap formation than normal donors. These results suggested that monitoring the percentages of CRL that are capable of ST complex-C3 receptor cap formation may be a good indicator of the success of chemotherapy of CLL patients. This has now been verified by sequential studies of individual CLL patients undergoing observation and treatment over the course of several months.

Fluctuations in WBC or lymphocyte counts failed to provide a consistently reliable index of the effectiveness of chemotherapy in CLL. The percentage of CRL capable of ST complex-C3 receptor cap formation was a much more reliable index of therapy. In general, CLL patients possessing at least 41 percent of ST complex-C3 receptor cap-forming CRL after 15 min at 37° C. represented a good clinical picture, regardless of WBC, percentage of lymphocytes, or other white-cell information, whereas patients forming ST complex-C3 receptor caps on fewer than 41 percent of CRL generally presented a clinical profile requiring chemotherapy.

Similar correlations between chemotherapy and capping of PBL con A receptors in CLL patients have been noted by Ben-Bassat et al. in Blood 55: 205–213 (1980). The relationship between response to chemotherapy and C3 receptor capping observed herein is consistent with, and extends, recent suggestions by others that response to therapy may be a good prognostic indicator in CLL, e.g., see Binet et al. in Cancer 40: 855–864 (1977); Johnson et al. in Clin. Haemat. 6: 237–244 (1977); Sawitsky et al. in Blood 50: 1049–1059 (1977); Liepman and Votaw in Cancer 41 1664–1669 (1978); and Burghouts et al. in Acta. Hemat. 63: 217–221 (1980).

Since mobility of cell-surface receptors in the plane of the cell membrane appears to be a ubiquitous characteristic of many types of normal cells, it appears likely that the increased percentages of lymphocytes incapable of cap formation in CLL reflect increased numbers of abnormal, non-functional B lymphocytes. Two different mechanisms may be involved in increasing the percentages of cap-forming CRL in successfully treated CLL patients. First, selective killing of the abnormal, non-capping B cells by chemotherapeutic agents may take place resulting in a relative enrichment in normal B cells. Second, it is possible that treatment with at least some chemotherapeutic agents may enhance capping by converting the impaired B lymphocytes into functional or partially functional cells. While present data do not permit the degree of contribution of these two possible mechanisms to be determined, the results of treating CLL lymphocytes with pharmacologic agents in vitro show that the percentage of capping can be increased to essentially normal levels in CLL PBL preparations by CLC (and, in some instances, by DMSO). These results provide evidence that it is possible for non-capping lymphocytes to be converted into normally capping cells in vitro by certain drugs; that such increases in capping ability may well be reflected by concomitant increases in CLL B lymphocyte functionality is suggested by the fact that impaired in vitro CLL PBL mitogenic responses can be reversed by DMSO, as reported by A. J. Dennis et al. in Ann. N.Y Acad. Sci. 243: 73-80 (1975).

Since CLC is known to interact with tubulin, preventing its polymerization into intact microtubules, the present results suggest that an impairment exists in the microtubule-cytoskeletal system of the majority of CLL B lymphocytes. Since this abnormality can be corrected by disrupting microtubules by exposure to CLC, it appears that intact microtubules inhibit capping of STM complex-C3 receptor on CLL lymphocytes. This conclusion is strengthened by the observation that lumicolchicine (lumiCLC) had no significant effect on C3 receptor capping in CLL and normal PBL. LumiCLC is similar to CLC in its biologic effects, differing from CLC essentially only in that it has no microtubule-disrupting properties. Small, but significant, increases in the percentages of cells capable of ST complex-C3 receptor capping can be obtained in the presence of $5 \times 10^{-5}$M CLC in the case of normal human PBL and mouse spleen lymphocytes. These small percentages of lymphocytes that are incapable of ST complex-C3 receptor cap formation in normal humans and in mouse spleen lympocytes may represent a small number of immature B lymphocytes in peripheral blood and spleen. The elevated numbers of B lymphocytes in CLL blood may represent immature B lymphocytes which have not yet developed capping ability and which are incapable of normal function.

It has now been found that variations in receptor capping of B lymphocytes are related to the progress of therapy for disorders affecting such cells, particularly chronic lymphocytic leukemia. Patietns who were clinically improving as a result of therapy showed increased C3 receptor capping, while most untreated CLL patients and those who were refractory to therapy failed to undergo C3 receptor capping. Thus, C3 receptor capping appears clinically useful for helping clinicians decide whether a given type of therapy is appropriate and/or whether the patient is responding or not.

The above-described capping method can also be used to study the effectiveness of chemotherapy of lymphocytic lymphoma patients; the situation is similar to that of CLL patients.

Analagous methods can be employed in a different assay procedure, i.e., for the detection of Fc receptors, particularly with the use of ST bacteria or other receptor-activating substances in place of erythrocytes. Fc receptors are entirely different from C3 receptors, but may occur on overlapping lymphocyte populations (some lymphocytes have both Fc and C3 receptors, some have only Fc, others have only C3, and many have neither). Fc receptors recognize and bind to the Fc piece of immunoglobulin G (Fc gamma receptors) or to the Fc piece of immunoglobulin M (Fc $\mu$ receptors). These Fc receptors occur on populations of various types of leukemic cells and on normal cells; they form rosettes which exhibit capping just like the previously described ST rosettes.

Kits can easily be prepared using heat-killed receptor-activating substances, preferably ST bacteria, optionally (in the case of gram-negative bacteria, which self-activate C3) coated with C3-activating antibodies, for clinial laboratory use in monitoring the efficacy and/or appropriateness of chemotherapy in CLL patients. Similarly, kits for Fc gamma and Fc $\mu$ receptor capping tests can be made. These kits could simultaneously be used to detect Fc and C3 receptors on individual cells.

One useful kit example contains both fluorescein-labeled C3 receptor and rhodamine-labeled Fc gamma receptor reagents. After mixing with lymphocytes and removal of unbound materials, microscope slide preparations can be viewed under a fluorescence microscope; cells having only yellow-green (fluorescein) are C3 receptor positive; cells with red fluorescence (rhodamine) are Fc gamma receptor positive, and cells bearing both yellow-green and red are positive for both C3 and Fc gamma receptors. Using a third fluorochrome to label Fc $\mu$ receptor cells (or another set of similarly labeled reagents), one can simultaneously determine Fc gamma, Fc $\mu$ and C3 receptors by choosing as a third reagent one which fluoresces a different, third color.

Alternatively, one can label C3d activators with fluorescein and C3b activators with rhodamine and determine simultaneously on individual cells those possessing either C3b or C3d receptors or both. Many possible combinations similar to the above are possible.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight. All data were compared by the unpaired Student's t-test, and are expressed as the mean±one SE of multiple determinations.

EXAMPLE 1

Preparation of *Salmonella typhi* or *Salmonella typhimurium*

ST cultures were maintained on blood agar plates with transfer to fresh plates every 2-3 months. The bacteria were grown overnight at 37° C. by inoculation of trypticase soy broth with a loop of fresh overnight ST culture using conventional methods for the cultivation of this well known organism. ST were heat-killed (60° C., 60 min.), washed 3× with veronal buffered-saline (VBS), and then incubated with a predetermined subagglutinating dose of rabbit anti-ST IgM antibody to produce a particulate antigen-antibody complex, which was washed 3× with VBS and then incubated with a predetermined amount of 1:5-VBS diluted fresh mouse serum as a source of complement.

The particulate antigen-antibody complexes (referred to herein as ST complexes, containing activated C3) were washed 3× in RPMI-1640 containing 1 percent bovine serum albumin (BSA), counted, adjusted to $10^8$ cells/ml with the same medium, aliquoted, and frozen for future use.

EXAMPLE 2

Preparation of C3d-specific complexes

Incubation of ST and the above IgM antibodies thereto with mouse complement at 37° C. for 10 min. prior to washing produces ST complexes which bind to both C3b and C3d receptors, as has been reported by S. Pincus et al. in Blood 40: 303 (1972). However, if the incubation time at 37° is extended to 40 min., ST complexes are formed which bind only to C3d receptors on human lymphocytes, affording for the first time easily prepared reagents which are specific to this C3 receptor.

The C3d specificity of such complexes was shown by the fact that the bind to CLL peripheral blood lymphocytes (PBL), which is consistent with reports that CLL patients have elevated levels thereof, usually possessing C3d and not C3b receptors. The complexes do not bind to human erythrocytes, which are known to have C3b receptors but not C3d receptors. Additionally, these complexes bound to 99 percent of Raji lymphoblastoid cells (which contain C3b as well as C3d receptors) and to 93 percent of Daudi lymphoblastoid cells, which bind only C3d.

EXAMPLE 3

Fluorescent Conjugation of ST Complexes

Fluorescein- or rhodamine-conjugated ST were sensitized with rabbit IgM antibody and fresh mouse serum according to the methods described by Gormus et al. in Cell. Immunol. 55: 94–105 (1980) and J. Immunol. 124: 2747–2753 (1975). Alternatively, the ST cells of the complexes can be labeled by using similarly conjugated rabbit IgM antibodies against the ST bacteria.

ST complexes can be initially labeled with fluorescein or rhodamine, and rosetted preparations thereof can then be studied in combination with other, different markers, e.g., fluorescent antibody or Fc receptor rosettes and/or autoradiography. Thus, individual cells can now be studied for the simultaneous presence of C3 receptors in combination with other fluorescent or non-fluorescent markers.

EXAMPLE 4

Preparation of Human Peripheral Blood Lymphocytes (PBL)

Human peripheral blood lymphocytes were isolated from heparinized blood of normal volunteers and from patients with CLL or lymphocytic lymphoma by dextran (3 percent in saline) sedimentation, incubation of the leukocyte-rich plasma with 20 mg/ml carbonyl iron (GAF Corp., New York, N.Y.) and centrifugation on Ficoll-Hypaque gradients described by A. Boyum et al. in Scand. J. Clin. Lab. Invest. 21 (Suppl. 97): 77–87 (1968). By morphology criteria (Wright's stain), the interface layer contained greater than 99 percent lymphocytes. Viability of lymphocyte preparations was greater than 98 percent by trypan blue exclusion. Patients from a hematology clinic were selected at random, with no prior knowledge of their history or clinical status.

EXAMPLE 5

Rosette Formation with Human Lymphocytes

Human leucocytes containing complement-rosetting lymphocytes (CRL) were adjusted to $10^7$ per ml with RPMI-1640-1 percent BSA, and one volume (usually 0.1 ml) mixed with an equal volume of thawed ST complex. After 30 min. of incubation at 0.5° C. (crushed ice), rosetted and non-rosetted cells were freed of unbound ST complex by twice centrifuging at 125xG for 15 min. at 4° C. Controls prepared from complement-free ST and ST/antibody preparations failed to produce significant rosetting of CRL cells.

ST complexes formed rosettes with 14.3±0.74 percent of normal human peripheral blood lymphocyte samples (n=58) and with 42.4±3.1 percent of CLL peripheral blood lymphocyte samples (n=44) ($p<0.0005$).

EXAMPLE 6

Capping of Human Peripheral Blood Lymphocytes

Capping was initiated by transferring aliquots of cold, ST complex-rosetted CRL to a 37° C. water bath. Control cells were maintained in ice throughout. Aliquots of 37° C.-incubated cells were transferred to an ice bath at time intervals and, along with control aliquots, were fixed immediately by the addition of an equal volume of fresh, ice-cold glutaraldehyde (Tousimis Corp., Rockville, MD) diluted to 5 percent in RPMI-1640. Cells were allowed to fix in cold 2.5 percent glutaraldehyde for at least 15 min, and then for a minimum of 2 h at room temperature before being pelleted onto microscope slides by a cytocentrifuge (Shandon Scientific Co., Sewickley, PA). Unlike erythrocyte-based rosettes, the ST complexes thus fixed can be stored indefinitely prior to slide preparation and study.

The slides were dehydrated for 5 min in 95 percent ethanol and cover-slipped with a mixture containing 1 part phosphate-buffered saline, pH 7.2, and 9 parts glycerine. Coverslips were sealed with clear fingernail polish. Rosetted and capped lymphocytes were enumerated by alternate phase contrast and fluorescence microscopy utilizing a Zeiss fluorescence microscope equipped with epi-illumination; at least 300 cells were examined per slide. A cell was considered rosette-positive if three or more ST complexes were bound, and a rosetted lymphocyte was considered capped if ST complexes were localized to approximately one-third or less of the cell surface. Since essentially all rosetted cells bound many more than three ST complexes, problems were seldom encountered in categorizing rosetted CRL.

EXAMPLE 7

Pharmacological Modification of Capping

A stock solution of 0.01M colchicine (CLC) (Calbiochem, La Jolla, CA) in RPMI-1640 was freshly prepared before each experiment, and dilutions were made in RPMI just prior to use. Lumicolchicine (lumiCLC) was prepared by UV-irradiation in 95 percent ethanol according to the procedure of Wilson and Friedkin described in Biochemistry 5: 2463–2468 (1966), and was diluted in RPMI for capping studies. Stock solutions of 0.01M cytochalasins A (CA) and B (CB) (Aldrich Chemical Co., Milwaukee, WI) were prepared in dimethyl sulfoxide (DMSO) and stored at 4° C. Stock solutions of CA and CB were diluted to the desired concentrations in RPMI immediately before use.

Washed, centrifuged cell pellets containing CRL-ST complex rosettes prepared at 0.5° C. were suspended in iced drug-containing solutions and incubated at 0.5° C. for 1 h. After this incubation, zero time aliquots of cells were fixed in 2.5 percent glutaraldehyde. The experimental tubes were transferred to a 37° C. water bath and controls were left in ice; glutaraldehyde was added to aliquots at timed intervals.

Multiple concentrations of CLC and CB were tested on normal lymphocytes to determine the concentration of each agent giving optimal activity. Maximal augmentation of capping occurred at $5\times10^{-5}$M CLC, while maximum inhibition of normal PBL ST complex-C3 receptor capping (with minimal cell disruption) occurred at $2.5\times10^{-5}$M CB in 0.25 percent DMSO- RPMI. These optimal reagent concentrations were subsequently utilized for study of CLL peripheral blood lymphocyte-C3 receptor capping. Cell viabilities were determined by trypan blue exclusion to determine if the observed effects of the tested pharmacologic agents were due to cell death. In all experiments >95 percent of drug-treated cells remained viable.

Studies were also performed on normal human PBL to test capping of C3 receptors after removal of drugs by washing. Full recovery of normal capping occurred after incubation of washed, CB-treated lymphocytes for 30 min at 37° C. CA was identical to CB in its ability to inhibit ST complex-C3 receptor capping of normal human peripheral blood lymphocytes and of mouse spleen lymphocytes. Treatment of ST complex-CRL rosettes with drugs did not alter the final percentages of rosetted cells compared to untreated controls.

EXAMPLE 8

Diagnosis and Clinical Staging of Disease

For patient samples employed in diagnostic testing, diagnostic criteria for CLL were peripheral blood lymphocytosis (greater than $15 \times 10^6$/ml) and a hypercellular bone marrow with lymphocytes constituting at least 50 percent of nucleated cells. Clinical responses to therapy were based upon changes in: (1) peripheral blood lymphocytosis; (2) palpable lymphadenopathy, hepatomegaly, or splenomegaly; (3) anemia or thrombocytopenia; and (4) subjective criteria including weakness or fever unrelated to infection. A positive therapeutic response was defined as a resolution of all subjective symptoms of CLL together with definite improvement in at least two of the remaining criteria.

Patients were staged according to the system described by Rai et al. in Blood 46: 219-234 (1975). Briefly, the stages are defined in terms of lymphocytosis alone (stage O) or in combination with either of the following: lymphadenopathy (stage I); enlarged liver or spleen (stage II); anemia (stage III); or thrombocytopenia (stage IV).

No direct relationship between the Rai classification of CLL patients and capping was observed. Both group A (refractory) and group B (untreated) patients failed to cap, whereas >83 percent (5 of 6) of group A patients were Rai stage III or IV, and <8 percent (1 of 13) of group B patients were Rai III or IV. Also, CLL groups C and D (those giving a positive clinical response to therapy) were both capable of significant capping, but contained an essentially even distribution of Rai stage I-IV patients. That group B (untreated) contained mainly early Rai stage patients, and group a (refractory) contained mainly late Rai stages (Table I) is not surprising.

The following Table shows the relationship of this classification to the above A-D categories. Five to six group A (refractory) patients fell into the Rai stage III or IV categories, and 12 and 13 group B (untreated) patients were Rai stage O, I, or II. Groups C and D patients (positive clinical responders) contained an even distribution of Rai classes, i.e., 10 of 19 stage I or II, and 9 of 19 stage III or IV patients.

TABLE

RELATIONSHIP OF DISEASE STAGE TO CATEGORIES OF CLL PATIENTS

| Rai Stage | Patient category (No. of patients) | | | |
|---|---|---|---|---|
| of disease | A | B | C | D |
| 0 | 0 | 7 | 0 | 0 |
| I | 0 | 3 | 4 | 1 |
| II | 1 | 2 | 3 | 2 |
| III | 1 | 1 | 2 | 1 |
| IV | 4 | 0 | 5 | 1 |
| Totals | 6 | 13 | 14 | 5 |

No attempt was made in this study to determine whether one type of chemotherapeutic regimen was superior to another in terms of clinical response or of capping. Patients showing a good clinical response to therapy generally showed increased percentages of CRL capable of significant cap formation; however, few of the patients studies attained the mean normal level of CRT cells capable of cap formation.

EXAMPLE 9

Clinical Evaluation of Capping

Capping of C3 receptors of PBL from normal donors was first compared with that observed in PBL from 35 CLL patients. Capping of CLL C3 receptors was impaired at each of the times observed after transfer to 37° C. Because of the large variation in CLL capping at 37° C., data from patients were examined individually for intra-group stratification. Since 41 percent was the lowest number of ST complex-C3 receptor cap-forming CRL observed in normal donors after incubation at 37° C. for 15 min, this figure was used as a cut-off point. Two subgroups of patients were thus identified. Group I was composed of patients capable of ST complex-C3 receptor cap formation on at least 41 percent of the CRL cells; Group II failed to form caps on at least 41 percent of the CRL cells after 15 min of incubation at 37° C. The degree of ST complex-C3 receptor capping at 37° C. in Group II patients was not significantly different from that of normal PBL ice controls.

When the clinical charts of these patients were sudied, a relationship between therapy and C3 receptor capping ability became apparent, and four categories of patients could be operationally defined: (A) those currently undergoing chemotherapy, but who remained refractory to treatment; (B) those whoe had never received chemotherapy; (C) patients who were previously treated successfully, but who were not receiving therapy at the time of study (i.e., having clinically stable disease, and/or those who were clinically asymptomatic); and (D) patients currently undergoing treatment at the time of study and showing a good positive response (i.e., those who subsequently became asymptomatic or clinically stable and were later removed from chemotherapy). The chemotherapeutic agents used to treat the CLL patients studies herein included chlorambucil, prednisone, vincristine, cytoxan, and combinations of these drugs.

When the patients were grouped into one of these four categories, according to clinical results, it was seen that the group of patients who were unable to form ST complex-C3 receptor caps (Group II) contained patients who were refractory to all forms of ongoing therapy and those who had never received therapy for CLL. CLL patients who were capable of cap formation (Group I) were found to be both those with stable disease following previous successful treatment and those showing a good response to current, ongoing therapy. These observations indicate that the percentages of C3 receptor cap-forming CRL cells are closely related to the clinical response of the patients to treatment.

EXAMPLE 10

White Blood Counts

There was a wide range of white blood count (WBC) in each of the four categories, the patients undergoing successful current chemotherapy having the lowest mean WBC. However, there was no statistical difference between the mean WBC among the four categories of patients studied. Significant differences were observed in the mean absolute numbers of total lymphocytes among the four patient groups, but no consistent relationship to capping or to treatment could be discerned, except that those undergoing successful, current chemotherapy possessed the lowest total number of lymphocytes.

EXAMPLE 11

Complement-Rosetting Lymphocytes Counts

Since it was possible that the absolute numbers of C3 receptor cap-forming cells might be a better indicator of response to chemotherapy than such percentages, the data were recalculated as C3 receptor cap-forming CRL per $\mu l$ of blood. The results showed that much more striking differences between the four categories were apparent when considering percentages rather than absolute numbers. Patients who were showing a favorable response to ongoing chemotherapy and who showed the largest percentage of C3 receptor cap-forming CRL possessed approximately 4,500 cap-forming CRL/$\mu l$ of blood. This number was not significantly different from the corresponding values for patients who were refractory to ongoing chemotherapy (5,700/$\mu l$) or for those who had never previously been treated (6,200/$\mu l$).

Surprisingly, the previously treated patients who were asymptomatic or clinically stable, and who were receiving no chemotherapy at the time of study, possessed significantly larger absolute numbers of cap-forming CRL (8,700/$\mu l$ of blood) than the other three groups. The patients who were refractory to therapy possessed a mean of 30,700 CRL/$\mu l$ of blood, whereas each of the other three categories of CLL patients possessed significantly fewer absolute numbers of CRL; patients who were receiving current, successful chemotherapy possessed significantly fewer total CRL (8,200/$\mu l$ of blood) than the other categories of patients.

There were no statistically significant differences in the percentages of lymphocytes or of CRL among the four categories of patients, and none of the groups of patients studied approached normal values for any of the leukocyte parameters measured.

EXAMPLE 12

Cytoskeletal-Contractile Involvement in Capping

The next series of experiments examined the possibility of cytoskeletal-contractile involvement in C3 receptor capping by CLL lymphocytes. Since the effects of CLC (which disrupts microtubule integrity) and CA or CB (which disrupt microfilament integrity) on C3 receptor capping in mouse spleen lymphocytes and normal human PBL had already been determined, similar studies were undertaken utilizing PBL from many of the same CLL patients reported above. The previous studies showed that the optimal concentrations of these agents, using mouse spleen lymphocytes and normal human PBL ($5 \times 10^{-5}$M CLC and $2.5 \times 10^{-5}$M CB in 0.25 percent DMSO), enhanced capping slightly, but significantly, in normal donors and produced a marked degree of enhanced capping in each group of CLL patients studies. Capping of CLL C3 receptors was enhanced to levels equal to or exceeding that observed in normal donors in the presence of CLC, but LumiCLC ($5 \times 10^{-5}$M) had no effect on capping.

The results obtained in the presence of 0.25 percent DMSO/RPMI alone, or containing $2.5 \times 10^{-5}$M CB, depended on the category of CLL patients observed. In normal donors, total abolition of capping occurred in the presence of $2.5 \times 10^{-5}$M CB/0.25 percent DMSO/RPMI, whereas 0.25 percent DMSO/RPMI had no significant effect. In contrast, the patients who had never been treated for CLL showed enhanced capping in the presence of 0.25 percent DMSO/RPMI alone or containing $2.5 \times 10^5$M CB. Patients in remission, those responding favorably to current, ongoing therapy, and those who were refractory to chemotherapy were unaffected by 0.25 percent DMSO/RPMI alone or together with $2.5 \times 10^{-5}$M CB. Cytochalasin A (CA), which has microfilament disrupting properties similar to those of CB but lacks the ability to efficiently inhibit the transport of glucose across cell membranes, had effects on C3 receptor capping identical to CB.

EXAMPLE 13

In vitro Enhancement of Capping

Confirmation that impaired capping can be corrected in vitro was obtained in the study of untreated (group B) CLL patients in the presence of 0.25 percent DMSO or $2.5 \times 10^{-5}$M CB dissolved in 0.25 percent DMSO. This group of CLL patients showed a significant enhancement in ST complex-C3 receptor capping ability in the presence of these agents. CLL patients undergoing current successful chemotherapy, those in resmission after previous successful chemotherapy, and those who were refractory to chemotherapy were unaffected by 0.25 percent DMSO or by DB/0.25 percent DMSO.

In contrast, ST complex-C3 receptor capping in normal PBL and mouse spleen lymphocytes was unaffected by 0.25 percent DMSO, but was totally abolished by 0.25 percent DSMO containing $2.5 \times 10^{-5}$M CB. The data showed that CA and CB had identical abilities to inhibit C3 receptor capping. Since CA lacks the ability to inhibit the transport of metabolites across cell membranes but is equal to CB in microfilament disrupting ability, these results suggest that microfilaments in CLL CRL are not susceptible to disruption by CB at a concentration sufficient to totally disrupt normal CRL microfilaments and therefore that differences exist in CLL lymphocyte microfilaments as compared to normal donors.

There is no present explanation for the enhanced capping of ST complex-C3 receptor of PBL from untreated CLL patients in the presence of 0.25 percent DMSO; however, DMSO is known to have multiple effects on membranes and on the tertiary structure of proteins.

The preceding examples can be repeated with similar success by substituting the generally or specifically described reactants and/or operating conditions of this invention for those specifically used in the examples.

From the foregoing description, one skilled in the art to which this invention pertains can easily ascertain the essential characteristics thereof and, without departing from the spirit and scope of the present invention, can make various changes and modifications to adapt it to various usages and conditions.

INDUSTRIAL APPLICABILITY

As can be seen from the present specification and examples, the present invention is industrially useful in relating C3 and/or Fc receptor capping to clinical responses to therapy in patients with diseases, disorders, or malignancies involving cells that possess C3 and/or Fc receptors, respectively, particularly in monitoring the efficacy of therapy for chronic lymphoid leukemia.

What is claimed is:

1. A method for differentially diagnosing between human leukemia and lymphoma disorders involving leucocytes that possess at least three membrane receptors per leucocyte for one or more molecules selected from the group consisting of an activated third component of complement (C3), immunoglobulin G, and immunoglobulin M, which comprises:

(a) reacting a sample of a patient's blood containing leucocytes with particles coated with said molecules to form a complex;
   (b) incubating the complex under receptor cap forming conditions;
   (c) enumerating the percentage of leucocytes in said sample capable of forming receptor caps and
   (d) comparing said percentages to normals.

2. A method according to claim 1 wherein said particles are bacteria coated with molecules selected from the group consisting of activated third component of complement (C3), immunoglobulin G, and immunoglobulin M.

3. A method according to claim 2, wherein said particles are killed *Salmonella typhimurium* or *Salmonella typhi* bacteria.

4. A method according to claim 3, wherein said bacteria are labeled with a fluorescent or radioactive tagging agent.

5. A method according to claim 1 wherein said receptors are specific for: activated complement component C3d, Fc-gamma, or Fc-mu.

* * * * *